(12) United States Patent
Iwanaga

(10) Patent No.: US 9,226,659 B2
(45) Date of Patent: Jan. 5, 2016

(54) FUNDUS CAMERA

(75) Inventor: Tomoyuki Iwanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 335 days.

(21) Appl. No.: 13/210,975

(22) Filed: Aug. 16, 2011

(65) Prior Publication Data
US 2012/0044458 A1 Feb. 23, 2012

(30) Foreign Application Priority Data
Aug. 19, 2010 (JP) .................................. 2010-184281

(51) Int. Cl.
*A61B 3/12* (2006.01)
*A61B 3/14* (2006.01)

(52) U.S. Cl.
CPC .... *A61B 3/12* (2013.01); *A61B 3/14* (2013.01)

(58) Field of Classification Search
CPC ............ A61B 3/14; A61B 3/156; A61B 3/12; A61B 3/103; A61B 3/1015
USPC .......................... 351/200, 205, 206, 211, 246
See application file for complete search history.

(56) References Cited

U.S. PATENT DOCUMENTS

| 4,253,743 | A * | 3/1981 | Matsumura | 351/208 |
| 4,799,783 | A * | 1/1989 | Takahashi et al. | 351/206 |
| 4,834,526 | A * | 5/1989 | Nunokawa | 351/206 |
| 7,134,754 | B2 * | 11/2006 | Kerr et al. | 351/206 |
| 2004/0156016 | A1 * | 8/2004 | Kerr et al. | 351/206 |
| 2006/0077344 | A1 * | 4/2006 | Kashiwagi et al. | 351/206 |

FOREIGN PATENT DOCUMENTS

| JP | 03-032367 A | 2/1991 |
| JP | 09-131321 A | 5/1997 |

* cited by examiner

*Primary Examiner* — James Greece
(74) *Attorney, Agent, or Firm* — Canon U.S.A., Inc., IP Division

(57) ABSTRACT

A fundus camera according to the present invention includes a light metering unit configured to change a light metering area within an image captured by an imaging unit based on one of a position and a size of a light blocking member, and a controlling unit configured to control an amount of light emission from a light source based on a light metering value corresponding to the light metering area.

11 Claims, 10 Drawing Sheets

FUNDUS CAMERA

BACKGROUND OF THE INVENTION

1. Field of the Invention

The present invention relates to light amount control of illumination light in a fundus camera, and more specifically, to a light metering area used to control an amount of illumination light.

2. Description of the Related Art

Conventional fundus cameras are configured to set a predetermined amount of light to use according to when the camera changes a photographing method, such as a color photographing mode and a visible fluorescent photographing mode, or performs microcoria photographing, or changes a magnification ratio of photographing.

In the field of fundus camera, technology to control an amount of light for photographing by detecting return light from a fundus is also known.

As an example of the control technology, Japanese Patent Publication No. 03-032367 discusses a fundus camera which receives light reflected from a fundus at a plurality of points located in an area having a diameter larger than that of an optic disk and determines an amount of exposure so as not to be affected by the optic disk portion.

Japanese Patent Application Laid-Open No. 09-131321 discusses an ophthalmological examination apparatus that changes a reference value of an amount of light to be received during fluorescence imaging according to insertion and removal of an excitation filter and a barrier filter to/from an optical path.

In these fundus cameras, if a subject's eye has a pupil of a small diameter, a light blocking member is switched to one of a smaller size so that illumination light can reach the fundus of the eye. In this case, however, the illumination light reflected at the cornea and the crystalline lens of the eye may appear as a flare at the peripheral part of a fundus image to be obtained. In addition, the switching of the light blocking members may cause changes in brightness distribution of the fundus image.

A brightness distribution of a fundus image varies depending on the ways of focus adjustment, one way with a focus target projected onto a fundus, and another way without use of the focus target. Thus, insertion and removal of a focus target may affect light metering values to be used.

SUMMARY OF THE INVENTION

Aspects of the present invention relate to improvements in the accuracy of light amount control by changing a light metering area based on at least one of a position and a size of a light blocking member.

According to an aspect of the present invention, a fundus camera includes an illumination optical system configured to guide light from a light source to a fundus, a light blocking member configured to block the light emitted from the light source, an imaging unit configured to capture an image using light returned from the fundus through a photographic optical system, a light metering unit configured to change a light metering area within the image captured by the imaging unit based on at least one of a position and a size of the light blocking member, and a controlling unit configured to control an amount of light emission from the light source based on a light metering value corresponding to the light metering area.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
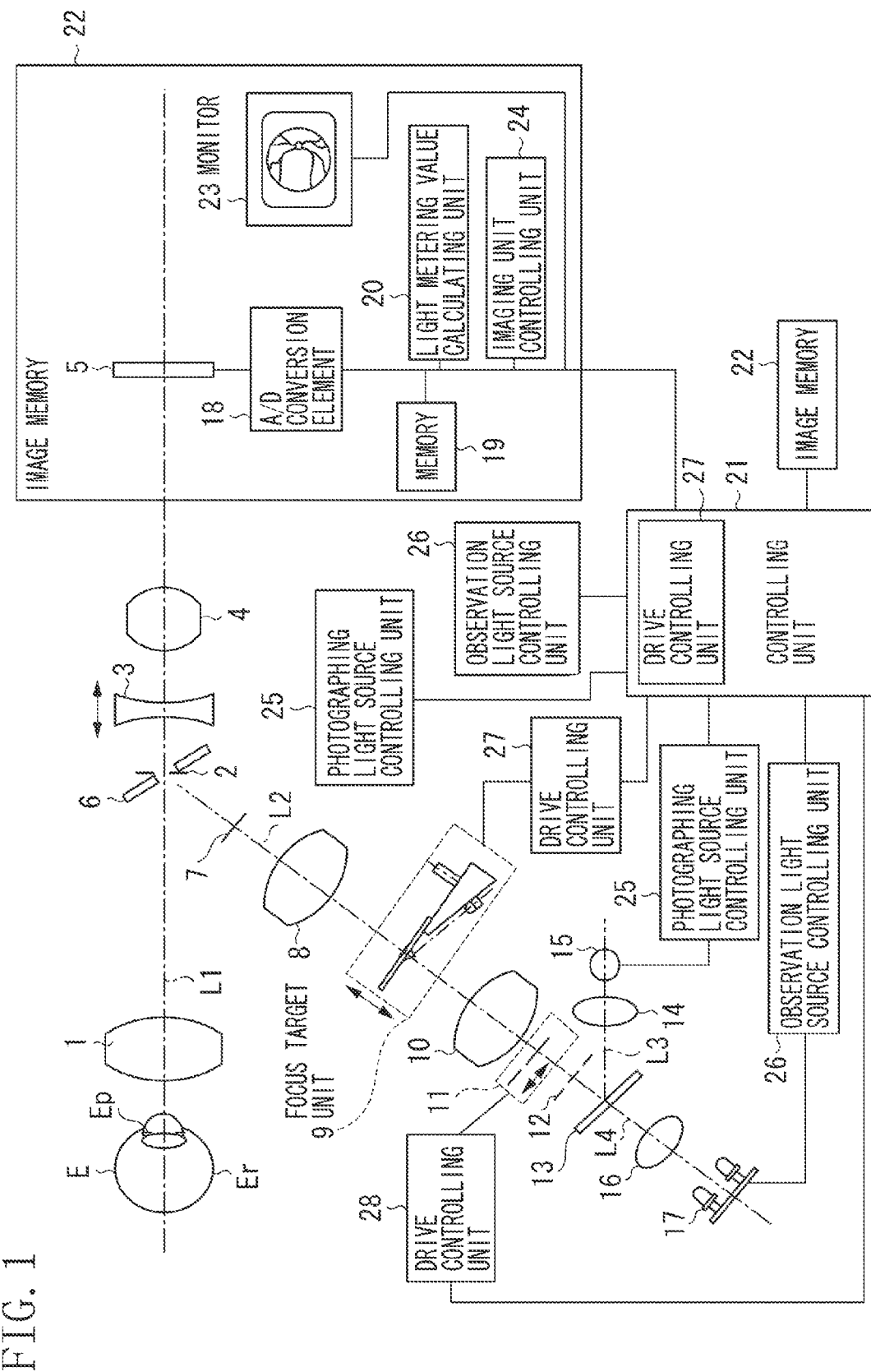
FIG. 1 illustrates a configuration of a fundus camera according to a first exemplary embodiment of the present invention.

FIG. 1 illustrates a configuration of a fundus camera according to a first exemplary embodiment.

The fundus camera includes an objective lens 1 to be located facing to a subject's eye E, and a diaphragm 2, a focusing lens 3, and an imaging lens 4 are arranged in sequence on an optical axis L1 of the objective lens 1. A sensor serving as an image capturing unit includes an imaging device 5 that is sensitive to visible light and infrared light. The objective lens 1, the diaphragm 2, the focusing lens 3, and the imaging lens 4 constitute a photographic optical system to perform observation and photographing on a fundus.

The fundus camera further includes a perforated mirror 6 that is arranged near the diaphragm 2 at an angle relative to the optical axis L1. A cornea baffle 7 that has a light blocking point at its center and a lens 8 are arranged on an optical axis L2 extending along a direction to which light reflected by the perforated mirror 6 travels. Along the optical axis L2, a focus target unit 9, a lens 10, and a ring slit 12 having a ring-shaped opening are arranged.

Along the optical axis L2, a crystalline lens baffle 11 and a dichroic mirror 13 are also arranged. The crystalline lens baffle 11 serves as a light blocking member having a size-changeable light blocking point. The dichroic mirror 13 has characteristics to transmit infrared light, but reflects visible light. The focus target unit 9 is arranged in a manner to be movable along the optical axis L2 and retractable from the optical axis L2.

The cornea baffle 7, the crystalline lens baffle 11, and the ring slit 12 are, respectively, arranged to positions optically approximately conjugated with the cornea, the rear surface of the crystalline lens, and the pupil Ep of the subject's eye E, through the objective lens 1, the lens 8, and the lens 10.

The dichroic mirror 13 has an optical axis L3 along which light reflected by the dichroic mirror 13 travels. Along the optical axis L3, a condenser lens 14, and a flash lamp source 15 that emits visible light pulses for photographing are arranged. The dichroic mirror 13 has an optical axis L3 along which light passes therethrough. Along the optical axis L4 of the dichroic mirror 13, a condenser lens 16 and an infrared light-emitting diode (LED) 17 are arranged. The infrared LED 17 is an observation light source including a plurality of infrared LEDs that each emits infrared stationary light.

These components between the objective lens 1 and the dichroic mirror 13, the condenser lens 14, and the condenser lens 16 constitute an illumination optical system to illuminate a fundus. Through the illumination optical system, light emitted from the flash lamp source 15 and the infrared LED 17 illuminates a fundus.

In the present exemplary embodiment, the above-described optical systems are encased in one housing to form a fundus camera optical unit as a whole. The fundus camera optical unit is mounted on a slidable mount (not illustrated), so that the fundus camera optical unit can be positioned in alignment with the subject's eye E.

An output from the imaging device 5 serving as an imaging unit is converted by an analog-to-digital (A/D) conversion element 18 into a digital signal, stored in a memory 19, and output to a light metering value calculating unit 20. Each of these components is connected to a controlling unit 21 such as a central control unit (CPU) that generally controls the fundus camera. The controlling unit 21 is connected to an image memory 22 where still images captured by the imaging device 5 are stored as digital images.

The fundus camera further includes a monitor 23, and an imaging unit controlling unit 24 to display images observed using infrared light and images photographed using visible light captured by the imaging device 5.

The flash lamp source 15 is connected to a photographing light source controlling unit 25. The infrared LED 17 is connected to an observation light source controlling unit 26. These units 25 and 26 transmit and receive control signals to and from the controlling unit 21.

The focus target unit 9 is connected to a focus target drive controlling unit 27 configured to control the movement of the focus target unit 9 along the optical axis L2 and the insertion and removal of the focus target unit 9 to/from the optical axis L2. The crystalline lens baffle 11 is connected to a crystalline lens baffle drive controlling unit 28 configured to control change in the size of the light blocking point of the crystalline lens baffle 11. The focusing lens 3 is connected to a focusing lens drive controlling unit 29 configured to control a drive of the focusing lens 3 to move along the optical axis L1. These drive controlling units 27 to 29 transmit and receive signals to and from the controlling unit 21.

The controlling unit 21 is further connected to an operation unit 30 and a photographing switch 31 to be controlled by the controlling unit 21. The operation unit 30 is used to set conditions for inserting and removing the focus target unit 9 and for changing the size the crystalline lens baffle 11.

The fundus camera operates as follows.

In the fundus camera, light emitted by the infrared LED 17 is condensed by the condenser lens 16, passes through the dichroic mirror 13, and is restrained into a ring-shaped light flux by the ring slit 12 and the crystalline lens baffle 11. The restrained ring-shaped light passes through the lens 10, the lens 8, and the cornea baffle 7, and once forms an image of the ring slit 12 on the perforated mirror 6 and also is reflected by the perforated mirror 6 into the direction along the optical axis L1.

The light passes through the objective lens 1, and again forms an image of the ring slit 12 near the pupil Ep of the subject's eye E, to illuminate the fundus Er of the subject's eye E. At this point, an image of the cornea baffle 7 is formed near the cornea of the subject's eye E, and an image of the crystalline lens baffle 11 is formed near the rear surface of the crystalline lens.

Meanwhile, the infrared LED 17 emits stationary light to illuminate the fundus Er. Return light from the fundus Er (i.e., a reflected and scattering light flux) exits the subject's eye E from the pupil Ep to pass the objective lens 1, the diaphragm 2, the focusing lens 3, and the imaging lens 4 to reach the imaging device 5, where an image of the fundus is captured. The captured image is converted into digital signals by the A/D conversion element 18, so that a fundus observation image is displayed on the monitor 23 via the imaging unit controlling unit 24.

Figure 2:
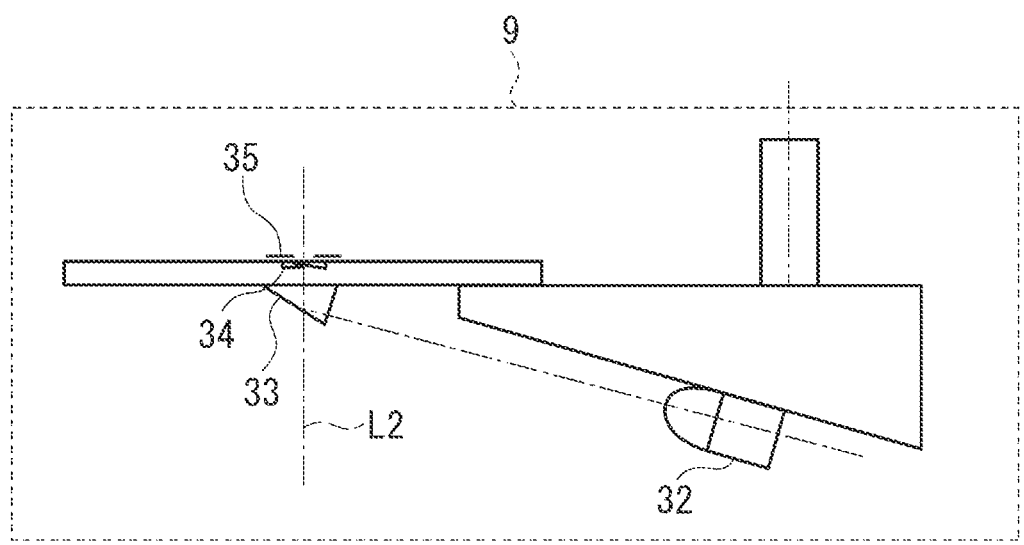
FIG. 2 illustrates a focus target unit.

FIG. 2 illustrates the focus target unit 9.

The light emitted from the infrared LED 32 is deflected by a prism 33 into a direction along the optical axis L2. The light is divided by a pair of micro prisms 34 that have faces sloping at angles opposite to each other into two light fluxes travelling along two directions. The divided light fluxes are restrained by a rectangular opening of a focus target mask 35. The light fluxes enter the lens 8 and are reflected by the perforated mirror 6 to travel to the fundus Er of the subject's eye E through the objective lens 1.

Figure 3:
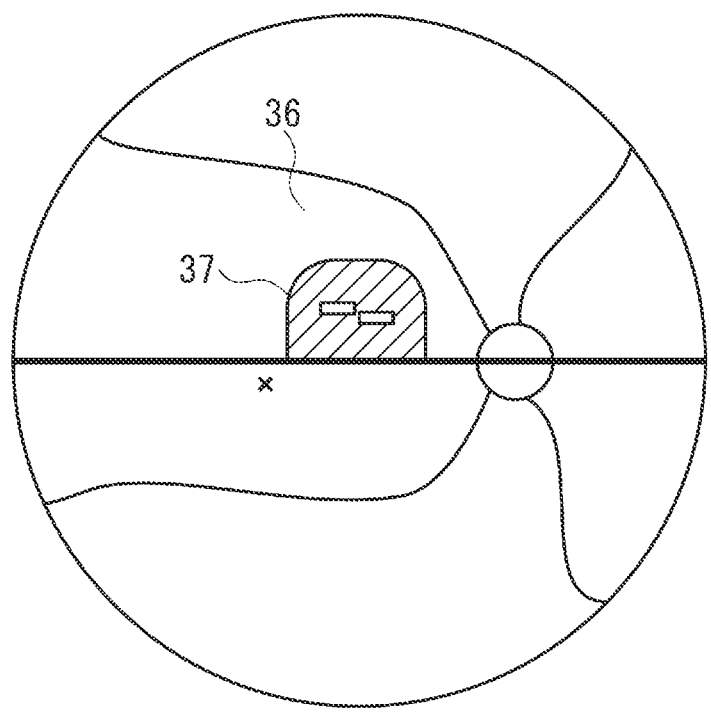
FIG. 3 illustrates a fundus image and a focus target image.

FIG. 3 illustrates a fundus image 36 and focus target images 37 of the subject's eye E displayed on the monitor 23. The focus target images 37 each contain a dark area in which illumination light emitted from the infrared LED 17 for illuminating the fundus Er is partial blocked by the focus target mask 35 and a bright area illuminated by the light flux that is emitted from the infrared LED 32 and passes through the rectangular opening of the focus target mask 35. The focus target images 37 are projected onto the fundus image 36.

An examiner manipulates an operation stick (not illustrated) while observing the fundus image 36 displayed on the monitor 23, so that the subject's eye E is positioned in alignment with the fundus camera optical unit. The examiner further observes the focus target images 37 and manipulates a focusing knob (not illustrated), so that the focus target images 37 are arranged in a line.

In the present exemplary embodiment, the controlling unit 21 is configured to control the focus lens drive controlling unit 29 to drive the optical axis 1 of the focusing lens 3 to a position corresponding to a control value calculated by the focus target drive controlling unit 27. Such operation enables the examiner to arrange the focus target images 37 in a line, which completes focusing.

Figure 4:
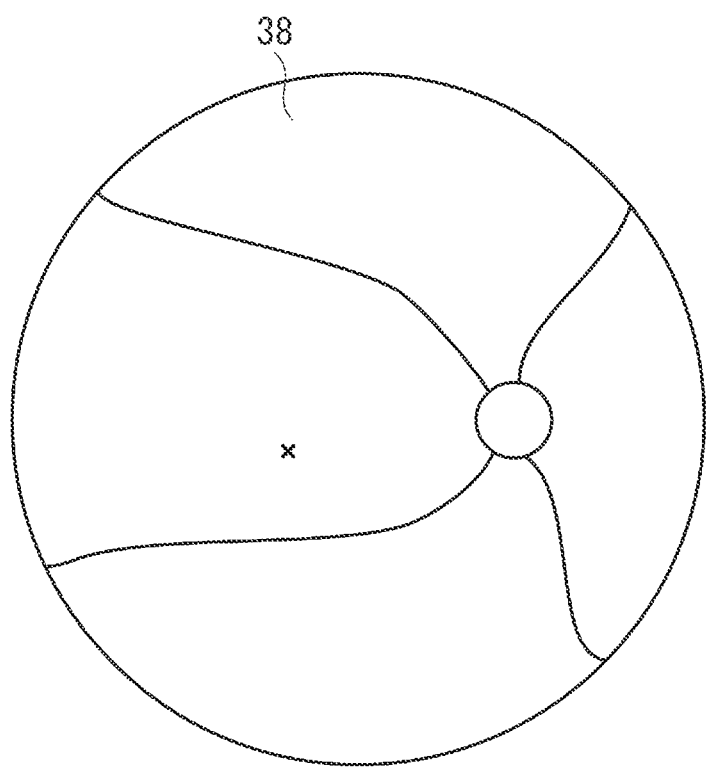
FIG. 4 illustrates a fundus image captured with a focus target unit being positioned off an optical axis.

The examiner can retract the focus target unit 9 from the optical axis L2 using the operation unit 30 when desiring to observe the part he/she currently cannot observe due to the focus target images 37 within the fundus image 36 of the subject's eye E. FIG. 4 illustrates a fundus image 38 displayed on the monitor 23 when the focus target unit 9 is retracted from the optical axis L2.

Automatic light amount controls of the infrared LED 17 and the flash lamp source 15 are described. The infrared LED 17 is an observation light source, and the flash lamp source 15 is a photographing light source in the present exemplary embodiment.

First, the automatic light amount control in a state in which the focus target unit 9 is inserted to the optical axis L2 is described.

The light from the infrared LED 17 illustrates the fundus Er of the subject's eye E as described above, and the reflected and scattering light from the fundus Er reaches a two-dimensional sensor that is an imaging unit including the imaging device 5, and forms an image. The image is converted by the A/D conversion element 18 into digital signals. Subsequently, the light metering value calculating unit 20 determines a light metering area in response to information from the controlling unit 21 indicating whether the focus target unit 9 is positioned on or off the optical axis L2, and calculates a light metering value from the determined light metering area.

The controlling unit 21 receives the calculated light metering value, and compares it with a reference value to calculate a control value, so that the infrared LED 17 is controlled by the observation light source controlling unit 26 to obtain an observation image of appropriate brightness.

When the photographing switch 31 is pressed, the controlling unit 21 calculates a control value to obtain appropriate brightness of a fundus image captured by the flash lamp source 15, based on the light metering value calculated by the light metering value calculating unit 20 and the control value set by the observation light source controlling unit 26. The controlling unit 21, then, controls the focus target drive controlling unit 27 to retract the focus target unit 9 from the optical axis L2, and controls the photographing light source controlling unit 25 to cause the flash lamp source 15 to emit light.

The light emitted from the flash lamp source 15 is collected by the condenser lens 14, reflected by the dichroic mirror 13, and restricted by the crystalline lens baffle 11 and the ring slit 12 into a ring-shaped light flux.

The restrained ring-shaped light flux passes through the lens 10, the lens 8, and the cornea baffle 7, and once forms an image of the ring slit 12 on the perforated mirror 6, and is also reflected by the perforated mirror 6 into the direction along the optical axis L1. Further, the light passes through the objective lens 1, and again forms an image of the ring slit 12 near the pupil Ep of the subject's eye E, to illuminate the fundus Er of the subject's eye E.

The fundus Er reflects and scatters the light emitted from flash lamp source 15. The reflected and scattering light exits the subject's eye E from the pupil Ep, and passes through the objective lens 1, the diaphragm 2, the focusing lens 3, and the imaging lens 4, and reaches the imaging device 5 to form an image there. The image is converted by the A/D conversion element 18 into digital signals, which are stored in the image memory 22.

As described above, while the examiner observes the fundus Er of the subject's eye E, the examiner can retract the focus target unit 9 from the optical axis L2 using the operation unit 30 when desiring to observe the part of the fundus image 36 of the subject's eye E he/she currently cannot observe due to the focus target images 37.

At this point of time, the fundus image 38 illustrated in FIG. 4 is observed. The light metering value calculating unit 20 calculates a light metering value based on the area within the fundus image 38 except the dark and bright areas of the focus target images 37 when the focus target unit 9 is positioned on the optical axis L2. But if there is no focus target image 37 covering the fundus image 38, calculation based on a larger light metering area can improve the accuracy of light metering.

In this case, the examiner retracts the focus target unit 9 from the optical axis L2 to observe the area covered by the focus target images 37, so that the uncovered area is also added to the light metering area to be used for the calculation.

The controlling unit 21 controls an amount of light emission from the infrared LED 17 using the observation light source controlling unit 26 based on the light metering value calculated by the light metering value calculating unit 20. Further, the controlling unit 21 calculates a control value of the flash lamp source 15 based on the light metering value output from the light metering value calculating unit 20 and the control value set by the observation light source controlling unit 26, controls the photographing light source controlling unit 25, and causes the flash lamp source 15 to emit light to capture a fundus image.

As described above, the fundus illuminated by light from the infrared LED 17 is represented as images having different brightness distributions, such as the fundus images 36 and 38, according to whether the focus target unit 9 is inserted to or retracted from the optical axis L2.

Accordingly, the light metering value calculating unit 20 determines an appropriate light metering area for each position of the focus target unit 9, and calculates a light metering value. Thus, independently of the insertion or removal of the focus target unit 9, an accurate light metering value can be obtained. Further, the obtained light metering value is used to control the photographing light source controlling unit 25 to cause the flash lamp source 15 to emit light, so that a fundus image can be captured with adequate brightness.

An automatic light amount control in response to size change of the crystalline lens baffle 11 according to a second exemplary embodiment is described.

Figure 5:
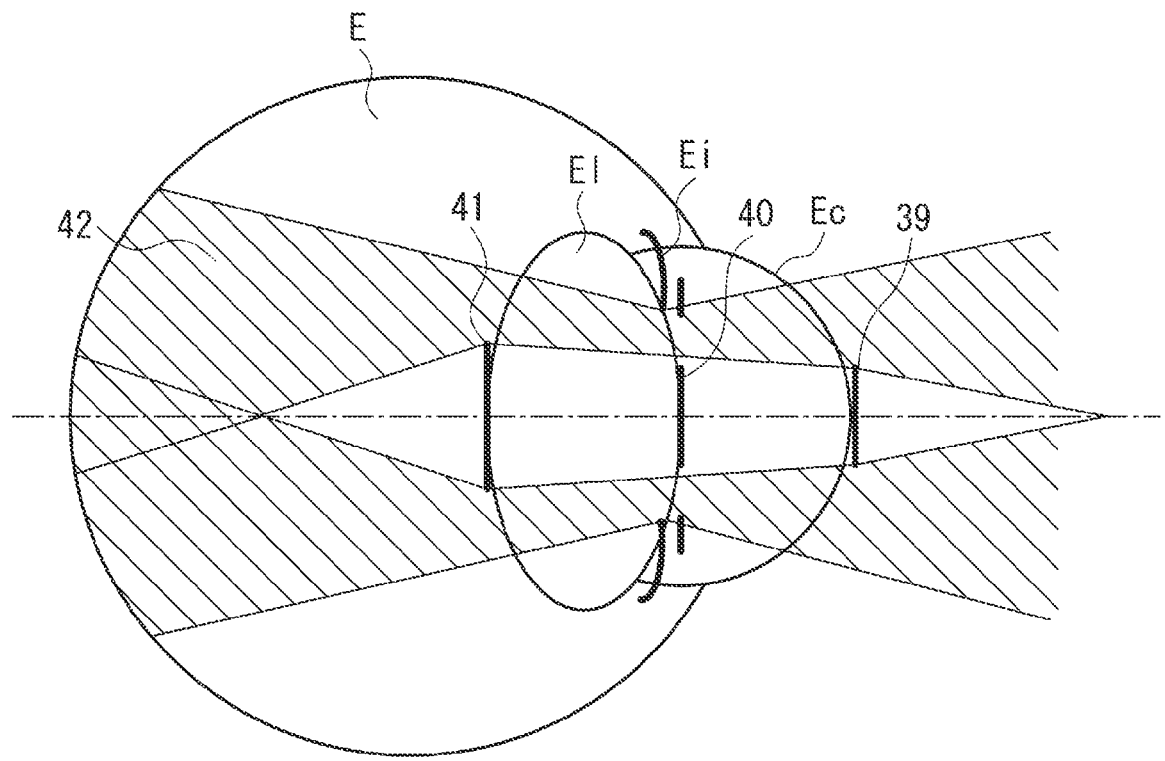
FIG. 5 illustrates a fundus of a subject's eye when illuminated with illumination light.

FIG. 5 illustrates a fundus of a subject's eye E that is illuminated by illumination light emitted from the infrared LED 17 or the flash lamp source 15.

In FIG. 5, a cornea baffle image 39 as an image of the cornea baffle 7 is formed near the cornea Ec of the anterior eye portion of the subject's eye E. A ring slit image 40 as an image of the ring slit 12 is formed near the front surface of the crystalline lens El. A crystalline lens baffle image 41 as an image of the crystalline lens baffle 11 is formed near the rear surface of the crystalline lens El. The iris Ei is located near the front of the crystalline lens El. These baffles are members are variable in sizes to remove reflected light from the anterior eye portion of the subject's eye E.

The cornea baffle image 39, the ring slit image 40, and the crystalline lens baffle image 41 are used to prevent reflection of illumination light at the optical surfaces of the subject's eye E, so that the illumination light 42 (shaded parts in FIG. 5) passes around the cornea baffle image 39, the ring slit image 40, and the crystalline lens baffle image 41, and illuminates the fundus.

Figure 6:
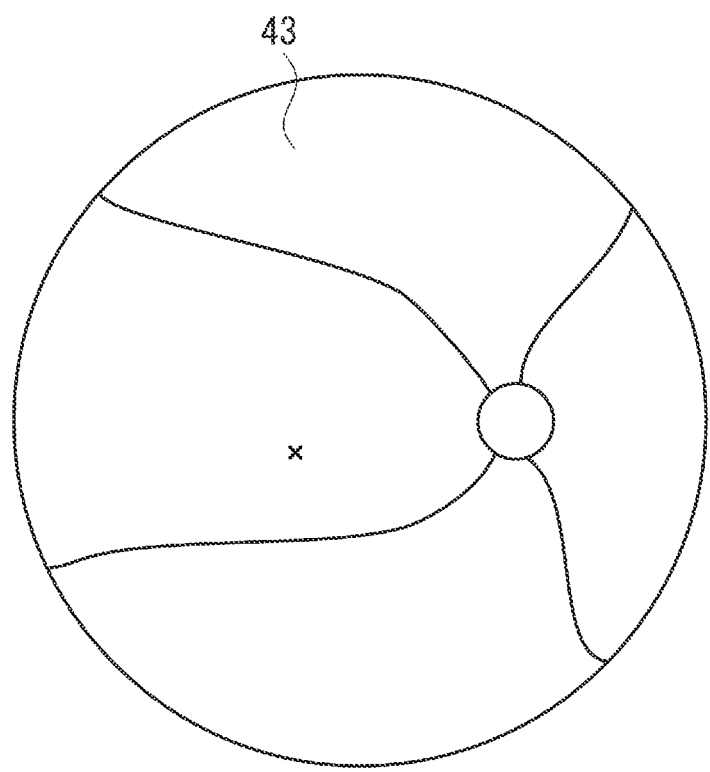
FIG. 6 illustrates a fundus image captured with a focus target unit being positioned off an optical axis.

FIG. 6 illustrates the fundus image 43 with the focus target unit 9 being retracted from the optical axis L2.

Figure 7:
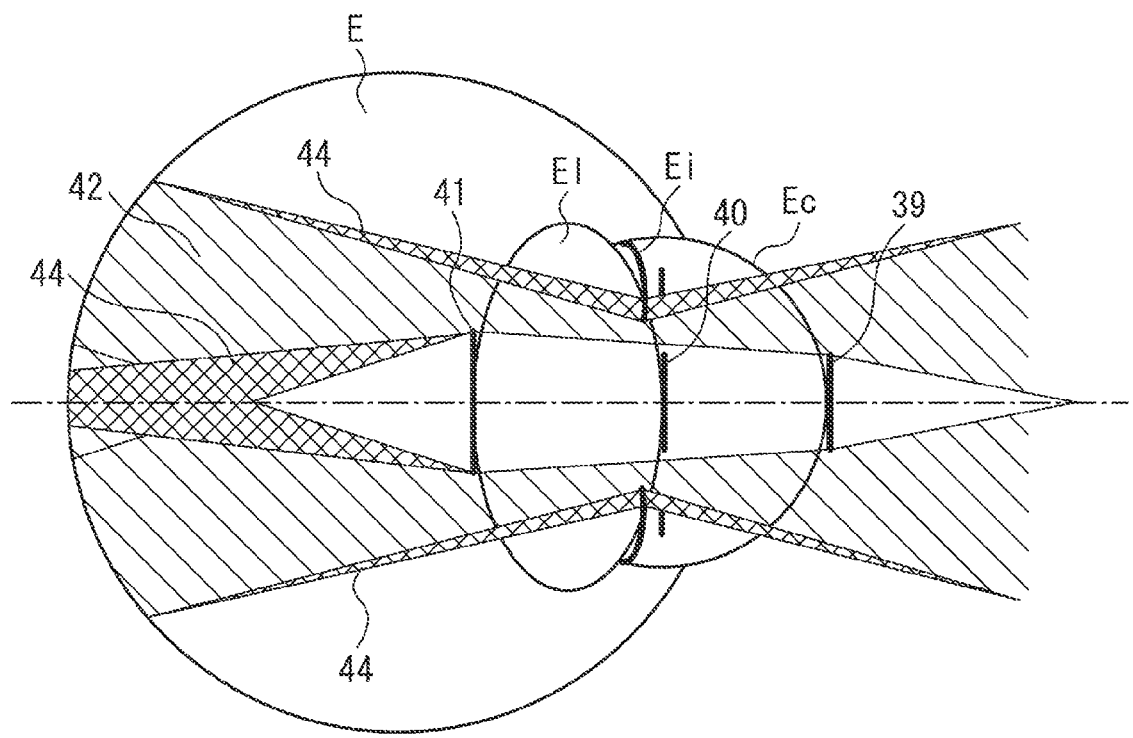
FIG. 7 illustrates a fundus of a subject's eye when the iris is constricted.

FIG. 7 illustrates a fundus of a subject's eye E illuminated by illumination light emitted from the infrared LED 17 or the flash lamp source 15, when the iris Ei of the subject's eye E is constricted and the pupil has a smaller diameter.

The constriction of the iris Ei generates an illumination light blocking area 44, which is illustrated as the mesh area in FIG. 7, in the illumination light 42 in FIG. 5, so that uneven illumination occurs on the fundus and the central area of the fundus cannot be illuminated with the light.

Figure 8:
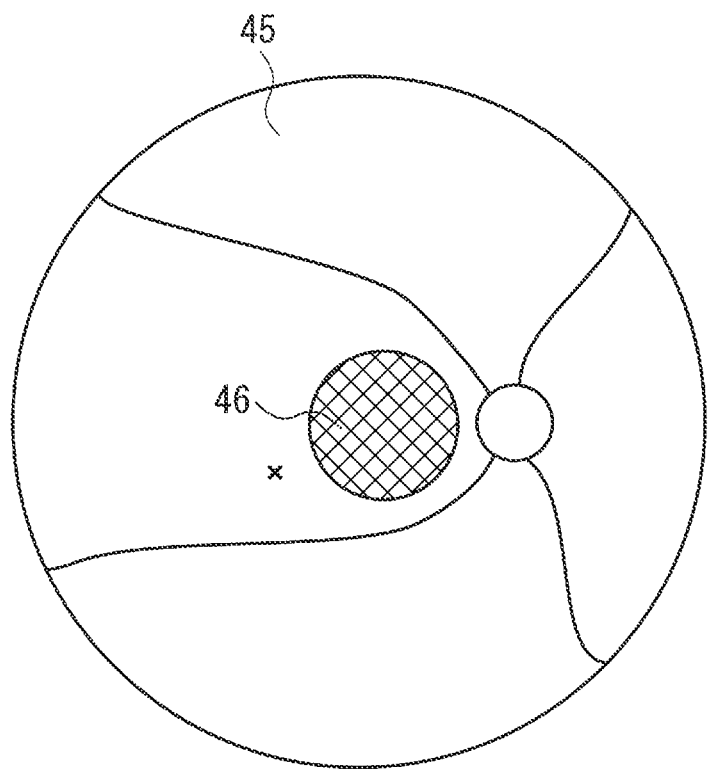
FIG. 8 illustrates a fundus image captured when the iris is constricted.

FIG. 8 illustrates a fundus image 45 captured when the iris Ei is constricted.

The mesh part at the center of the fundus image 45 illustrates uneven illumination 46 generated by the illumination light blocked by the iris Ei.

With such uneven illumination 46, the central area of the fundus image 45 cannot be observed or photographed with adequate brightness. Thus, in this case, the examiner manipulates the operation unit 30 to cause the controlling unit 21 to drive the crystalline lens baffle drive controlling unit 28, so that the crystalline lens baffle 11 changes its size. At the same time, the controlling unit 21 determines the size of the crystalline lens baffle 11 to be inserted into the optical system, based on the signal output from the drive controlling unit 28. The insertion into the optical system means that the member is inserted into at least part of an optical path of the optical system.

Figure 9:
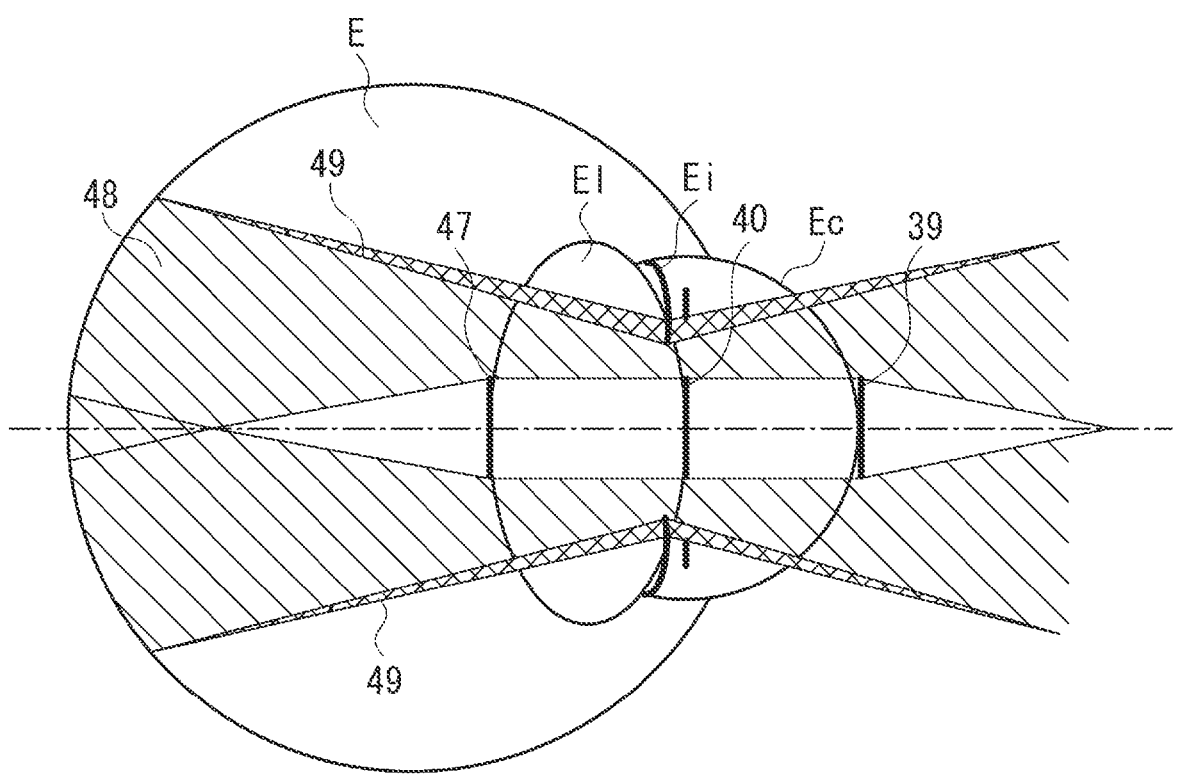
FIG. 9 illustrates a fundus of a subject's eye when illuminated with illumination light using a small crystalline lens baffle.

FIG. 9 illustrates a fundus of a subject's eye E when illuminated with illumination light emitted from the infrared LED 17 or the flash lamp source 15 after the size of the crystalline lens baffle 11 is switched to a smaller one.

The switched crystalline lens baffle 11 of a smaller size enables formation of a crystalline lens smaller-baffle image 47 near the rear surface of the crystalline lens El. Thus, the illumination light 48, which is illustrated by the shaded part, passes around the cornea baffle image 39, the ring slit image 40, the crystalline lens smaller-baffle image 47, and the iris Ei, and illuminates the central area of the fundus.

In this case, however, a shadowed area of the illumination light 48 due to the cornea baffle image 39, the ring slit image 40, and the crystalline lens smaller-baffle image 47 is reduced near the rear surface of the crystalline lens El. As a result, reflected light of the illumination light 48 at the rear surface of the crystalline lens appears in a fundus image to be observed or photographed at a higher probability as compared with the case in FIG. 5.

Figure 10:
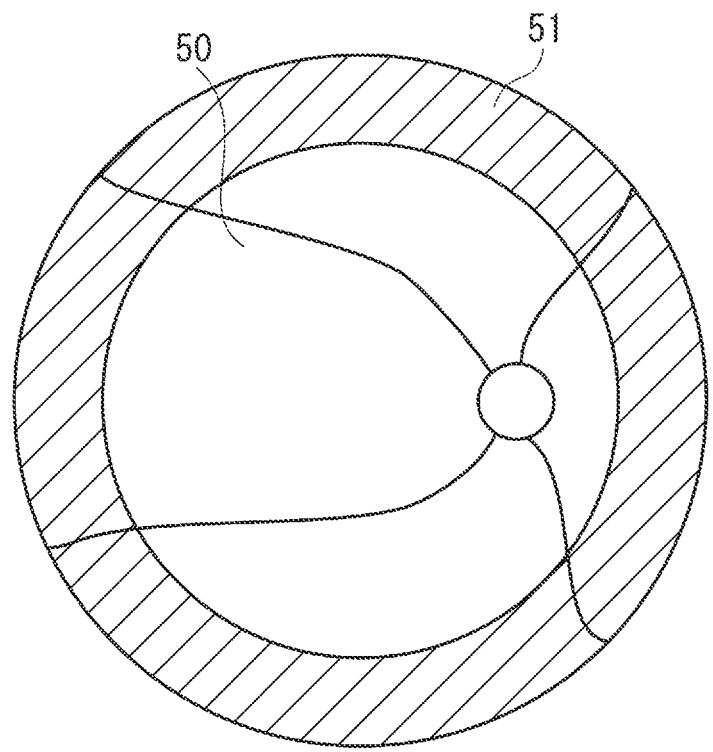
FIG. 10 illustrates a fundus image captured when a smaller crystalline lens baffle is used.

FIG. 10 illustrates a fundus image 50 of a subject's eye E when a smaller crystalline lens baffle 11 is used.

FIG. 10 contains a shaded area which is a flare 51 appearing at the periphery of the fundus image 50. The flare 51 is caused by the reflected light of the illumination light 48 at the rear surface of the crystalline lens because the smaller crystalline lens baffle 11 is used.

In this way, when a subject's eye E has a smaller pupil Ep, in other words, when the iris Ei is constricted, the examiner manipulates the operation unit 30 to change the size of the crystalline lens baffle 11 into a smaller one.

With the smaller crystalline lens baffle 11, light is emitted from the infrared LED 17 illuminates the fundus, and is reflected and scattered from the fundus to reach the imaging device 5 and form an image there. The image is converted by the A/D conversion element 18 to digital signals.

The light metering value calculating unit 20, then, determines the size of the crystalline lens baffle 11 based on information from the controlling unit 21 about the driving state of the crystalline lens baffle drive controlling unit 28. When the light metering value calculating unit 20 determines that a larger crystalline lens baffle 11 is used, the area of the fundus image 43 in FIG. 6 is set as the light metering area, whereas when the light metering value calculating unit 20 determines that a smaller crystalline lens baffle 11 is used, the area of the fundus image 50 in FIG. 10 except the flare 51 is set as the light metering area to calculate the light metering value.

The controlling unit 21 receives the calculated light metering value, compares it with the reference value to calculate the control value. The observation light source controlling unit 26, then, controls the infrared LED 17 to obtain an observation image of appropriate brightness.

When the photographing switch 31 is pressed, the controlling unit 21 calculates a control value to obtain appropriate brightness of a fundus image captured using the flash lamp source 15, based on the light metering value calculated by the light metering value calculating unit 20 and the control value set by the observation light source controlling unit 26. The controlling unit 21, then, controls the focus target drive controlling unit 27 to retract the focus target unit from the optical axis L2, and controls the photographing light source controlling unit 25 to cause the flash lamp source 15 to emit light.

The light emitted from the flash lamp source 15 is collected by the condenser lens 14, reflected by the dichroic mirror 13, and restricted by the crystalline lens baffle 11 and the ring slit 12 into a ring-shaped light flux. The restrained ring-shaped light flux passes through the lens 10, the lens 8, and the cornea baffle 7, and once forms an image of the ring slit 12 on the perforated mirror 6, and is also reflected by the perforated mirror 6 into the direction along the optical axis L1. Further, the light passes through the objective lens 1, and again forms an image of the ring slit 12 near the pupil Ep of the subject's eye E, to illuminate the fundus Er of the subject's eye E.

The fundus Er returns the light (i.e., reflected and scattering light flux) emitted from flash lamp source 15. The reflected and scattering light flux exits the subject's eye E from the pupil Ep, and passes through the objective lens 1, the diaphragm 2, the focusing lens 3, and the imaging lens 4, and reaches the imaging device 5 to form an image there. The image is converted by the A/D conversion element 18 into digital signals, which are stored in the image memory 22.

As described above, with relative to the fundus illuminated by light from the infrared LED 17, flare is caused at the periphery of a fundus image such as the fundus images 43 and 50 at different incidence rates according to the driving state of the crystalline lens baffle drive controlling unit 28. Accordingly, the light metering value calculating unit 20 determines whether to use the area where the flare 51 is caused more often as a light metering area, based on the driving state of the crystalline lens baffle drive controlling unit 28, and selects an appropriate light metering area for the state and calculates a light metering value.

The above approach makes it possible to obtain an accurate light metering value independently of the size of the crystalline lens baffle 11 that is arranged at an optically conjugate position with the anterior eye portion of a subject's eye E, so that the value can be used to control the photographing light source controlling unit 25 to cause the flash lamp source 15 to emit light to obtain a fundus image of appropriate brightness.

In the first exemplary embodiment, a light metering area is selected from a fundus image that is obtained by illumination with light from the infrared LED 17, based on the insertion and removal state of the focus target unit 9 on the optical axis L2, to calculate a light metering value. In the second exemplary embodiment, a light metering area is selected from a fundus image that is obtained by illumination with light from the infrared LED 17, based on the size of the crystalline lens baffle 11, to calculate a light metering value. However, when a light metering area is selected based on both of the insertion and removal state of the focus target unit 9 on the optical axis L2 and the size of the crystalline lens baffle 11 to calculate a light metering value, the light metering suitable for various conditions can be achieved. Accordingly, more accurate light amount control can be achieved in the infrared LED 17 as an observation light source and in the flash lamp source 15 as a photographing light source.

In the above described exemplary embodiments, the flash lamp source 15 is used as a photographing light source, but may be other sources such as a white LED. As described above, in a fundus camera according to aspects of the present invention, the accuracy of light amount control can be improved by changing a light metering area based on one of the position or the size of a light blocking member.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-184281 filed Aug. 19, 2010, which is hereby incorporated by reference herein in its entirety.

What is claimed is:

1. An ophthalmic apparatus, comprising:
an illumination optical system configured to guide light from a light source to a fundus;
a light blocking member configured to block at least a portion of the light emitted from the light source toward the fundus;
an imaging unit configured to capture an image using light returned from the fundus through a photographic optical system;
a light metering unit configured to change a light metering area within the image captured by the imaging unit based on at least one of a position and a size of the light blocking member; and
a controlling unit configured to control an amount of light toward the fundus through the light blocking member based on a light metering value corresponding to the light metering area changed by the light metering unit.

2. The ophthalmic apparatus according to claim 1, wherein the light blocking member is variable in size to block illumination light so as to prevent reflection of the illumination light at an anterior eye portion of a subject's eye by forming a buffle image thereon.

3. The ophthalmic apparatus according to claim 2, wherein the light blocking member is shiftably disposed in the illumination optical system and has a characteristic to block a part of the illumination light.

4. The ophthalmic apparatus according to claim 1, wherein the light blocking member is a projecting unit configured to project a focus target onto the fundus from the illumination optical system.

5. The ophthalmic apparatus according to claim 4, wherein the projecting unit is insertably and removably disposed in the illumination optical system.

6. The ophthalmic apparatus according to claim 1, further comprising a driving unit configured to change a size of the light blocking member, and
wherein the light metering unit changes the light metering area based on a signal output from the driving unit.

7. The ophthalmic apparatus according to claim 1, wherein the light source is one of an observation light source and a photographing light source.

8. The ophthalmic apparatus according to claim 2, wherein the light blocking member is a crystalline lens baffle.

9. An ophthalmic apparatus, comprising:
an illumination optical system configured to guide light from a light source to a fundus;
crystalline lens baffles which have a plurality of sizes and are configured to block at least a portion of the light emitted from the light source toward the fundus;
a driving unit configured to insert and retract the crystalline lens baffles having the plurality of sizes into and from the illumination optical system;
an imaging unit configured to capture an image using light returned from the fundus through a photographic optical system;
a light metering unit configured to change a light metering area within the image captured by the imaging unit according to the crystalline lens baffle inserted into the illumination optical system; and
a controlling unit configured to control an amount of light toward the fundus through the crystalline lens baffle based on a light metering value corresponding to the light metering area changed by the light metering unit.

10. An ophthalmic apparatus, comprising:
an illumination optical system configured to guide light from a light source to a fundus;
a projecting unit configured to project a focus target onto the fundus so as to form a focus target image for focusing operation;
a driving unit configured to insert and retract the projecting unit into and from the illumination optical system;
an imaging unit configured to capture an image using light returned from the fundus through a photographic optical system;
a light metering unit configured to change a light metering area within the image captured by the imaging unit according to the projecting unit inserted into the illumination optical system; and
a controlling unit configured to control an amount of light emission from the light source based on a light metering value corresponding to the light metering area changed by the light metering unit,
wherein, when the projecting unit is inserted into the illumination optical system, the projecting unit blocks at least a portion of the light emitted from the light source toward the fundus.

11. An ophthalmic apparatus, comprising:
an illumination optical system configured to guide light from a light source to a fundus;
crystalline lens baffles which have a plurality of sizes and are configured to block at least a portion of the light emitted from the light source toward the fundus;
a driving unit configured to select a size of the crystalline lens baffles according to an iris constriction of a subject's eye;
an imaging unit configured to capture a fundus image using light returned from the fundus through a photographic optical system;
a light metering unit configured to set a light metering area within the fundus image so as to be an area except a flare area caused by a reflected light at a rear surface of a crystalline lens in case that a smaller crystalline lens baffle is selected; and
a controlling unit configured to control an amount of light toward the fundus based on a light metering value corresponding to the light metering area set by the light metering unit.

* * * * *